United States Patent [19]

Smith, Jr. et al.

[11] Patent Number: 4,982,022
[45] Date of Patent: Jan. 1, 1991

[54] PROCESS FOR THE PREPARATION OF TERTIARY ALCOHOLS

[75] Inventors: Lawrence A. Smith, Jr., Bellaire; Robert P. Arganbright, Houston, both of Tex.

[73] Assignee: Chemical Research & Licensing Company, Houston, Tex.

[21] Appl. No.: 399,259

[22] Filed: Aug. 28, 1989

[51] Int. Cl.$^5$ ............... C07C 29/04; C07C 31/12; C07C 31/125
[52] U.S. Cl. .................................... 568/899
[58] Field of Search ........................ 568/899

[56] References Cited

U.S. PATENT DOCUMENTS

| | | | |
|---|---|---|---|
| 3,257,469 | 6/1966 | Kovach | 568/899 |
| 3,328,471 | 6/1967 | Kronig et al. | 260/641 |
| 4,087,471 | 5/1978 | Bowman et al. | 568/899 |
| 4,100,220 | 7/1978 | Bowman et al. | 260/683.15 R |
| 4,215,011 | 7/1980 | Smith et al. | 252/426 |
| 4,232,177 | 11/1980 | Smith et al. | 585/324 |
| 4,242,530 | 12/1980 | Smith et al. | 585/510 |
| 4,270,011 | 5/1981 | Okumura et al. | 568/899 |
| 4,302,356 | 11/1981 | Smith et al. | 252/477 R |
| 4,307,254 | 12/1981 | Smith et al. | 568/697 |
| 4,327,231 | 4/1982 | Okumura et al. | 568/899 |
| 4,336,407 | 6/1982 | Smith et al. | 568/697 |
| 4,439,350 | 3/1984 | Jones | 252/477 |
| 4,443,559 | 4/1984 | Smith et al. | 502/527 |
| 4,482,775 | 11/1984 | Smith et al. | 585/671 |
| 4,540,831 | 9/1985 | Briggs | 568/899 |

FOREIGN PATENT DOCUMENTS 102840 3/1984 European Pat. Off. ............ 568/899

*Primary Examiner*—J. E. Evans
*Attorney, Agent, or Firm*—Kenneth H. Johnson

[57] ABSTRACT

A process for the production of tertiary alcohols by the reaction of the corresponding isoolefin and water is disclosed. In particular the production of tertiary butyl alcohol and tertiary amyl alcohol is disclosed. The isoolefin and water are contacted over an acid cation exchange resin catalyst in a distillation column reactor where the products and reactants are separated by fractional distillation. In one embodiment a liquid level is maintained in the catalyst bed.

14 Claims, 2 Drawing Sheets

PROCESS FOR THE PREPARATION OF TERTIARY ALCOHOLS

BACKGROUND OF THE INVENTION

1. Field of the Invention

The present invention relates to a method for producing tertiary alcohols.

2. Related Art

Tertiary butyl alcohol (TBA) and tertiary amyl alcohol (TAA) have classically been synthesized in the past by reaction of sulfuric acid with the corresponding olefin to form the sulfate followed by hydrolysis. The use of sulfuric acid requires reconstitution of dilute acid by-product and the process is energy inefficient and corrosive. Recycle of the excess water, which contains some TBA, causes corrosion unless it is specially treated. Most of the TBA produced at present, however, is a by-product from the OXIRANE process for propylene oxide. In that process isobutane is oxidized to tho hydroperoxide which is then catalytically reacted with propylene to produce propylene oxide and TBA.

More recently TBA has been produced using an acid ion exchange resin to react isobutylene in a mixed C4 stream with water. See, for example U.S. Pat. Nos. 4,087,471 and 4,100,220. The resin catalyzed process is highly exothermic and is limited to equilibrium conversions, requiring separation of the TBA from excess water. U.S. Pat. No. 4,087,471 is specifically directed to the cooling aspect of the fixed bed reactor. Additionally, oligomers are produced as by-products, their production rate being determined by the amount of excess water used.

Recently a new method of carrying out catalytic reactions has been developed, wherein the components of the reaction system are concurrently separable by distillation, using the catalyst structures as the distillation structures, the method being commonly referred to as Catalytic Distillation. Such systems are described variously in U.S. Pat. Nos. 4,215,011; 4,232,177; 4,242,530; 4,302,356; 4,307,254; 4,336,407; 4,439,350; 4,443,559; and 4,482,775 commonly assigned herewith.

Briefly, a preferred and commercial catalyst structure described in the above patents comprises a cloth belt with a plurality of pockets spaced along the belt and containing particulate catalyst material, said cloth belt being wound in a helix about a spacing material such as stainless steel knitted mesh. These units are then disposed in the distillation column reactor. In addition, commonly assigned U.S. Pat. Nos. 4,443,559 and 4,250,052 disclose a variety of catalyst structures for this use and are incorporated herein.

SUMMARY OF THE INVENTION

Briefly, the present invention is a process for the production of tertiary butyl alcohol and tertiary amyl alcohol by contacting the corresponding olefin with water in a distillation column reactor containing a fixed bed acid ion exchange resin which acts as a catalytic distillation structure. The olefin and water react to form the alcohol in the acid ion exchange resin and at the same time the alcohol product is separated from the reactants by fractional distillation.

Because the alcohol products are generally higher boiling than the reactants or other components in the feed, the alcohols (tertiary butyl alcohol or tertiary amyl alcohol) distill down the column increasing the driving force because the reaction product has been removed and cannot contribute to the reverse reaction (Le Chatelier's Principle). Additionally, since the mixture is boiling in the bed the temperature of the reaction is controlled by the boiling point at the system pressure. The heat of reaction simply causes more boil up, but no increase in temperature.

As a result, a great deal of control over the rate of reaction can be achieved by regulating the system pressure. Also, adjusting through-put (residence time=liquid hourly space velocity[-1]) gives further control of the degree of olefin conversion.

The water concentration in the catalyst bed must be carefully controlled to keep the catalyst in the hydrated state and provide enough for the reaction and to accommodate the water azeotropes in the system. If too much water is used, the product alcohol will contain water and the reaction rate will decrease relative to the amount of excess water. If too little water is used, oligomerization of the $C_4$ or $C_5$ olefins occurs.

One method of controlling the correct amount of water is to measure the amount present in the alcohol fraction within the tower and to maintain that amount above zero but below the azeotropic concentration at the temperature and pressure used. Preferably, to insure that the catalyst is wetted, the catalyst bed should be operated in the flooded condition. That is, a liquid level should be maintained throughout the catalyst bed.

The term "liquid level" is used herein to mean an increased density of the material in the reaction distillation zone over that of a pure distillation as distinguished from a continuous liquid phase. The phase system as present in the reaction distillation zone is physically a froth. This is the result of the vapor traveling up through the liquid retained in the zone.

Another way of viewing this is that in normal distillation there is a vapor with liquid (internal reflux) trickling down through the vapor and contracting the catalyst whereas in the present "flooded" system the vapor is traveling up through a liquid phase to create the froth or foam. Hence in essence the benefits of the distillation are still obtained, i.e., separating the various components by the distillation whereas the increased liquid volume in contact with the catalyst improves the synthesis reaction.

The olefin containing stream is preferably introduced below the catalyst bed and the water above the bed. The alcohol product is withdrawn as bottoms and unreacted olefins (with any $C_4$ or $C_5$ inerts) and water free of alcohol taken overhead. The water may be then be recycled to the column without corrosion problems occurring.

Traditional catalytic structure, such as trays or inert packing may be used above and/or below the catalyst bed to insure the proper separation.

DETAILED DESCRIPTION OF THE INVENTION

Figure 1:
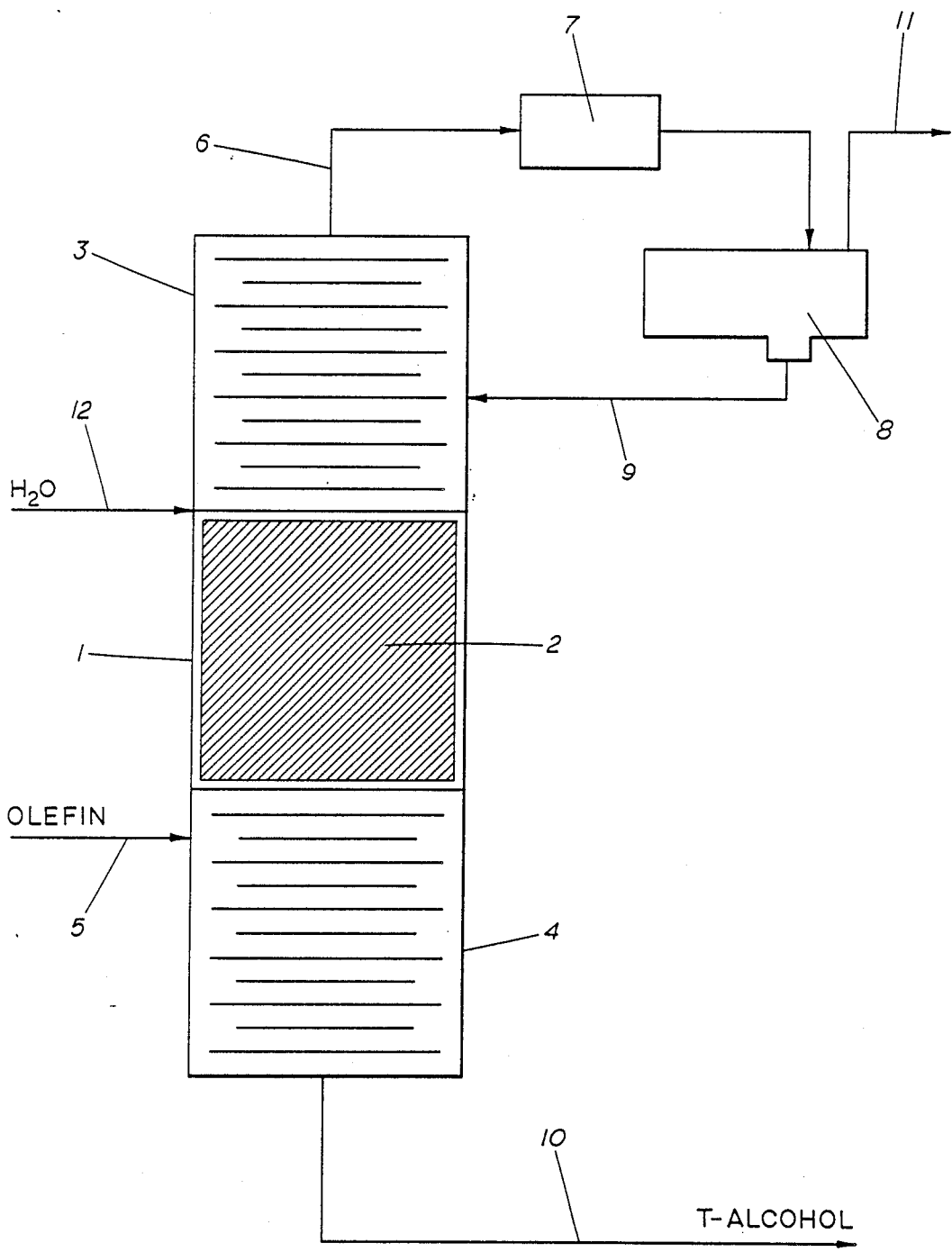
FIG. 1 is a schematic representation of one embodiment of the present invention.

In FIG. 1 there is shown a flow diagram of the distillation column reactor 1 configured to produce the tertiary alcohol from the hydration of the corresponding olefin. The olefin may be either isobutylene or isoamylene contained in a mixed C$_4$ or mixed C$_5$ stream commonly available. Such streams will generally be a mix of normal olefin and tertiary olefin, some corresponding alkane and some higher and lower hydrocarbon components. One of the advantages of the present process is that relatively low concentrations of tertiary olefins may be substantially removed from mixed streams. The normal and isoolefins are difficult to separate by distillation, hence the present process provides a means to make the separation and produce a valuable product, the alcohol, concurrently in a single procedure. Even with extremely dilute tertiary streams (<5 mole %) the reaction can be carried out, but economic considerations indicate that preferably there be at least 5 mole % of the tertiary olefin in the feed.

The distillation column reactor 1 may be divided into three sections. The middle section 2 contains the acid ion exchange resin catalyst bed supported as described in U.S. Pat. No. 4,215,011 which is hereby incorporated by reference. The top section 3 and bottom section 4 of the column contain standard distillation structure such as trays or inert packing.

Water 12 is fed to the distillation column reactor 1 at a point just above the catalyst bed 2. The olefin feed 5, either isobutylene or isoamylene, which may be contained in a mixed C$_4$ or C$_5$ stream is fed bed below the catalyst bed. The olefin reacts with the water in the catalyst bed to form the tertiary alcohol, TBA or TAA according to the olefin feed. The temperature in the catalyst bed is maintained at the boiling point of the mixture under the pressure in the column. Since the mixture is boiling and the alcohol is the higher boiling component, the alcohol liquid containing some dissolved water and olefin, flows down the column into the lower section of the column 4 where the separation of the product from the reactants is completed and remove via line 10. Since the reactant product, alcohol, is removed from the catalyst as soon as it is formed the reverse reaction is minimized allowing greater than normal equilibrium amounts of the product to be formed at the reaction conditions.

Likewise, as in normal distillation, the lower boiling components, water and olefin (and inert C$_4$'s or C$_5$'s) with some reaction product are distilled up the column where the separation is completed. Most of the tertiary olefin will preferentially react with the water to form the alcohol, but some dimerization is to be expected, the dimerized product, diisobutylene (DIB) or diisoamylene, will exit the column with the bottoms. Normal olefins will also distill overhead 6. Preferably a portion of the overhead, which is principally the unreacted hydrocarbons, may be condensed in condenser 7, and returned from accumulator 8 as reflux to the upper section 3 of distillation column reactor 1 via line 9 and the balance of the overhead removed via 11.

The distillation column reactor may be operated at subatmospheric, atmospheric or super-atmospheric pressure. The temperature in the bed will be the boiling point of the mixture at the operating pressure. The pressure will generally range from 15 psig to 300 psig with corresponding bed temperatures of 120° F. to 300° F., preferably from 130 to 200 psig and 140° to 200° F.

The water flow is adjusted to insure there is sufficient water to maintain the catalyst in the hydrated state and support the reaction to the tertiary alcohol. If too much water is used, the product will contain water. If too little is used, oligomerization of the olefin will occur. One method of controlling the necessary amount of water is to measure the amount of the water in the alcohol fraction within the lower section of the column and to maintain that amount above zero but below the azeotropic concentration at the temperature and pressure used.

Figure 2:
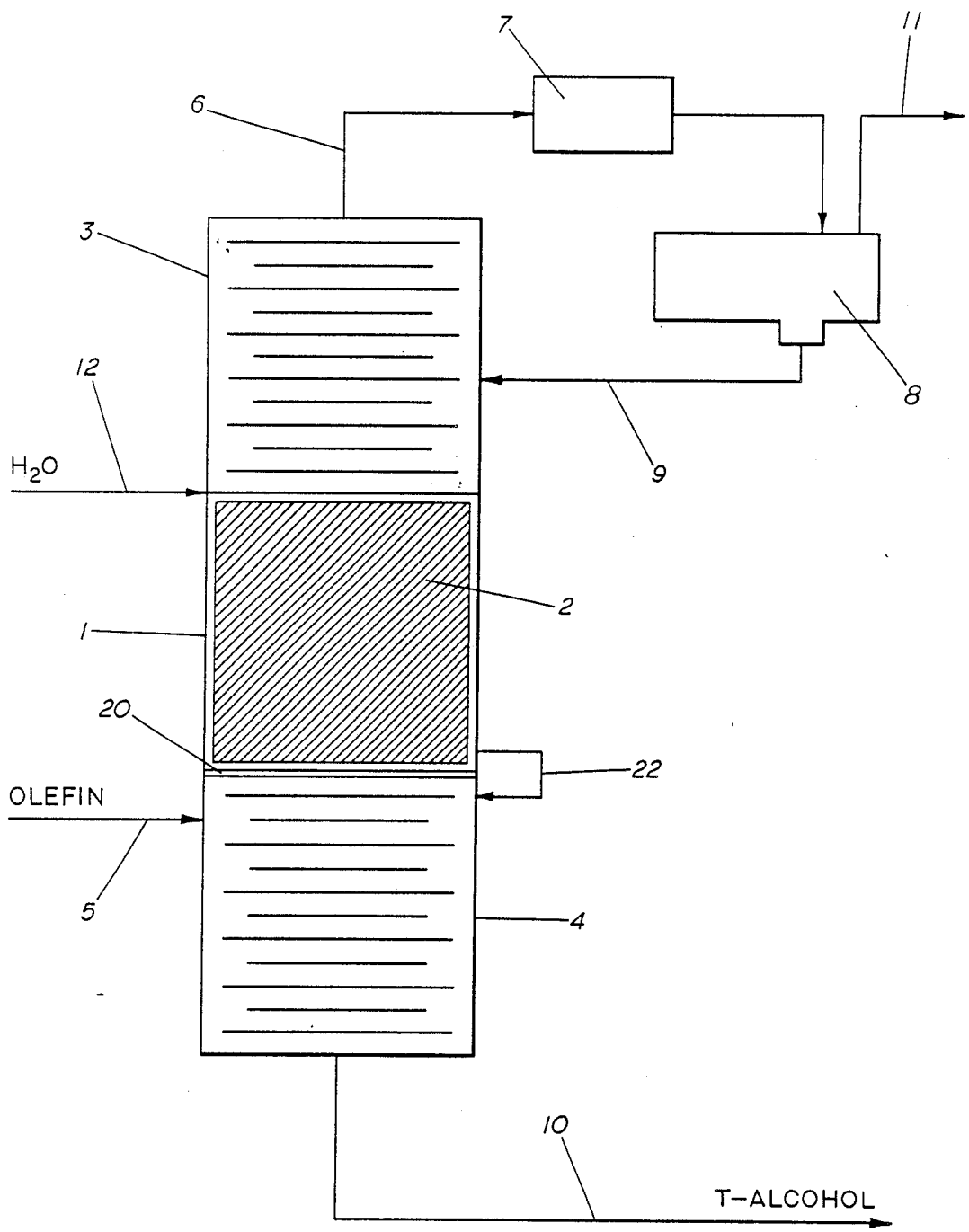
FIG. 2 is a schematic representation of a preferred embodiment of the present invention.

Preferably the catalyst bed portion 2 will be operated in the flooded condition as disclosed in commonly assigned co-pending patent application Ser. No. 07/328,487, which is herein incorporated by reference. As disclosed therein and shown in FIG. 2, which is basically the same as that of FIG. 1 wherein the liquid level may be maintained in the catalyst bed 2 by placing a liquid flow restrictor 20 directly below the catalyst. A liquid by pass line 22 around the restriction is used to control the liquid level as measured by the differential pressure across the catalyst bed or between the bottom of the catalyst bed and the top of the column. Another embodiment disclosed in Ser. No. 07/328,487, but not shown here, to obtain flooding of this type is division of the column as shown in present FIG. 1 into two columns with the catalyst bed 2 in one, conventional trays 4 in a second column and the liquid downflow from the catalyst bed to the conventional trays controlled through a flow control valve which acts as a liquid flow restriction between the two columns and maintains a desired preset liquid level in the catalyst bed (as by a differential pressure). Vapors of unreacted isoalkenes separated on the conventional trays 4 are carried by lines to any point in the catalyst bed, e.g., the bottom of that bed, just as if the vapors were rising directly unimpeded from the conventional trays below.

Such conventional items as valves, reboilers, slip streams, etc. are not shown, but would be obvious expedients to setting up such equipment.

Suitable acid cation exchange resins include those which contain sulfonic acid groups, and which may be obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethyl benzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenylether and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric and chlorosulfonic acid, or by copolymerizing aromatic compounds which contain sulfonic acid groups (see e.g., U.S. Pat. No. 2,366,007). Further sulfonic acid groups may be introduced into the polymer which already contain sulfonic acid groups; for example, by treatment with fuming sulfuric acid, i.e., sulfuric acid which contains sulfur trioxide. The treatment with fuming sulfuric acid is preferably carried out at 0° to 150° C. and the sulfuric acid should contain sufficient sulfur trioxide so that it still contains 10 to 50% free sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification No. 908,240). The ion exchange resin is generally used in a granular size of about 0.25 to 1 mm, although particles from 0.15 mm up to about 2 mm may be employed. The finer catalysts provide high surface area, but could also result in high pressure drops through the reactor requiring higher vapor velocities to agitate the catalyst. The macroreticular form of these catalysts have much larger surface area exposed and limited swelling which all of these resins undergo in a non-aqueous hydrocarbon medium compared to the gelular catalysts.

In this form the resins form too compact a bed and will not function adequately in a distillation, since there is a very large pressure drop through the bed and the free flow of internal reflux and rising vapor is impeded. Resins in the shape of conventional distillation structures, such as rings, saddles, and the like may be used in the present invention. The particulate resins may be employed by enclosing them in a porous container such as cloth, screen wire or polymeric mesh. The material used to make the container must be inert to the reactants and conditions in the reaction system. The cloth may be any material which meets this requirement such as cotton, fiber glass, polyester, nylon and the like. The screen wire may be aluminum, steel, stainless steel and the like. The polymer mesh may be nylon, teflon or the like. The mesh or threads per inch of the material used to make the container is such that the catalyst is retained therein and will not pass through the openings in the material. Particles of about 0.15 mm size or powders may be used and particles up to about ¼ inch diameter may be employed in the containers.

The container employed to hold the catalyst particles may have any configuration, such as the pockets disclosed in the commonly assigned patents above or the container may be a single cylinder, sphere, doughnut, cube, tube or the like.

Each container containing a solid catalytic material comprises a catalyst component. Each catalyst component is intimately associated with a spacing component which is comprised of at least 70 volume % open space up to about 95 volume % open space. This component may be rigid or resilient or a combination thereof. The combination of catalyst component and spacing component form the catalytic distillation structure. The total volume of open space for the catalytic distillation structure should be at least 10 volume % and preferably at least 20 volume % up to about 65 volume %. Thus desirably the spacing component or material should comprise about 30 volume % of the catalytic distillation structure, preferably about 30 volume % to 70 volume %. Resilient materials are preferred. One suitable such material is open mesh knitted stainless wire, known generally as demister wire or an expanded aluminum. Other resilient components may be similar open mesh knitted polymeric filaments of nylon, teflon and the like. Other materials such as highly open structures foamed material, e.g., reticulated polyurethane foam (rigid or resilient) may be formed in place or applied around the catalyst component.

In the case of larger catalyst components such as from about ¼ inch to ½ pellets, spheres, pills and the like each such larger component may be individually intimately associated with or surrounded by the spacing component as described above.

It is not essential that the spacing component, entirely cover the catalyst component. It is only necessary that the spacing component intimately associated with the catalyst component will act to space the various catalyst components away from one another as described above. Thus, the spacing component provides in effect a matrix of substantially open space in which the catalyst components are randomly but substantially evenly distributed.

A preferred catalytic distillation structure for use herein comprises placing the resin particles into a plurality of pockets in a cloth belt, which is supported in the distillation column reactor by open mesh knitted stainless steel wire by twisting the two together in a helical form. This allows the requisite flows and prevents loss of catalysts. The cloth may be any material which is inert in the reaction. Cotton or linen are useful, but fiber glass cloth or "Teflon" cloth are preferred.

In the following examples the catalyst packing consisted of bags in the form of a fiber glass cloth belt approximately six inches wide with narrow pockets approximately ¾ inch wide sewn across the belt. The pockets are spaced about ¼ inch apart. These pockets are filled with the catalyst particles to form approximately cylindrical containers, and the open ends are then sewn closed to confine the particles. This belt is then twisted into a helical form to fit inside the column. Twisted in with the belt is also a strip of an open mesh knitted stainless steel wire, which serves to separate the mole sieve filled cloth pockets and provide a passage for vapor flow.

The wire mesh provides the support for the catalyst (belt) and provides some degree of vapor passage through the catalyst particles, which otherwise form a very compact bed which has a high pressure drop. Thus, the down flowing liquid is in intimate contact with the rising vapors in the column.

In commercial-scale operations, it is contemplated, catalyst packing would be made up of alternating layers of mole sieve filled cloth belts similar to the ones described above, and a spacing material which could be of any convenient, suitable substance, such as a corrugated wire screen or wire cloth or a knitted wire mesh. The layers would be arranged vertically or horizontally. For simplicity of fabrication and for better distribution of vapor flow passages, a vertical orientation is preferred. The height of a section of this packing should be of any convenient dimension, from a few inches to several feet. For ease of assembly and installation, the packing would be made into sections of the desired shape and size, each section fastened together with circumferential bands of tie wires depending on its size and shape. A complete assembly in a column would consist of several sections, arranged in layers, with possibly the orientation of the catalyst-filled belts turned at right angles in successive layers to improve liquid and vapor flow distribution.

EXAMPLE 1

The reactor was a 1 inch, six foot stainless tube, composed of 2 foot sections bolted together. The bottom and top two feet contained conventional distillation packing, the middle two feet contained Amberlyst 15 resin in pockets (four pockets twisted with demister wire as described above). Water was fed under nitrogen pressure through a rotameter to the tower about 6"

above the top of the catalyst bed. The olefin, either isobutylene or isoamylene was fed from a tank to a point below the catalyst bed using a micrometering valve. The rate of feed of liquid olefin was adjusted to maintain the tower pressure with slow constant bleed of gas overhead. The rate of olefin addition was slightly larger than the rate of reaction. The water feed rate and bottoms withdraw rate are related. The water rotameter was set at a given value and the bottom withdrawal rate was adjusted to maintain a constant bottoms level.

Bottoms samples were analyzed by gas liquid phase chromatography using a 50 meter SE-30 capillary column and FID.

The conditions and results of several runs are set forth in TABLES I and II below.

TABLE I
PRODUCTION OF TERTIARY BUTYL ALCOHOL

| Run No. | A-II-46 | A1-1-48 | A-11-50 | A-11-52 |
|---|---|---|---|---|
| Temp., °F. | | | | |
| bottoms | 250 | 180 | 250 | 215 |
| cat. bed | 185 | 165 | 180 | 180 |
| overhead | no reflux | 162 | 176 | 180 |
| Pressure, psig | 160 | 140 | 185 | 225 |
| Analysis | | | | |
| Wt % isobutylene in feed | 100.0 | 42.5 | 42.4 | 10.2 |
| TBA in bottoms[1] | 41.3[3] | 98.9[2] | 98.3[3] | 96.8[3] |
| DIB in bottoms[1] | 42.6 | 0.2 | 0.7 | 3.2 |

[1]After vaporization of small amount of $C_4$'s from bottoms sample.
[2]Water layer was present in bottoms, analyzed by FID as 99.7% TBA, 0.3% unknown.
[3]No water layer was present.

TABLE II
PRODUCTION OF TERTIARY AMYL ALCOHOL

| Run No. | II-54 | II-55 |
|---|---|---|
| Temp., °F. | | |
| bottoms | 160 | 230 |
| cat. bed | 140–141 | 160–171 |
| overhead | 138 | 160 |
| Pressure, psig | 40 | 25 |
| Analysis, wt % | | |
| isoamylene in $C_5$ feed | 25 | 25 |
| $C_5$'s in bottoms | 78.9 | 71.6 |
| t-amyl alcohol in bottoms | 18.1 | 27.1 |
| dimers in bottoms | 3.0 | 0.3 |
| unknown | | 1.0 |

The equilibrium for the production of tertiary amyl alcohol is less favorable and control, in the laboratory tower, was more difficult than for TBA. This was probably due to a more stringent requirement for the water to $C_5$ olefin ratio in the catalyst bed.

EXAMPLE 2

While the conversion of isobutylene appeared to be satisfactory in the example above, it was found that the selectivity to TBA fell off rapidly. This has been attributed to mass transfer problems in wetting the catalyst to maintain it in the hydrated state. To achieve the desired hydration without excess of water, the tower was operated with a liquid level in the catalyst bed. A comparison was made with and without the liquid level in the bed as measured by the differential pressure across the catalyst bed. In the test runs, a 1" diameter tower was used ten feet in length. Four feet of Rohm and Haas Amberlyst 15 catalyst was inserted into the column in a pocketed belt twisted with wire mesh. The results are shown in TABLE III below.

TABLE III
PRODUCTION OF T-BUTYL ALCOHOL

| | Standard Process | Liquid in Catalyst Bed |
|---|---|---|
| Overhead pressure, psig | 160 | 165 |
| Feed Rates, ml/min. liq. | | |
| $C_4$'s (42% IB)[1] | 5.0 | 5.0 |
| $H_2O$ | 0.68 | 0.78 |
| Column Temp., °F. | | |
| Overhead | 168 | 165 |
| Cat. Zone | 165 | 185 |
| Bottoms | 230 | 315 |
| [2]Diff. Press. Across Cat. Zone | 0.0 | 72 |
| Bottoms analysis, wt. % | | |
| Lt. Ends ($C_4 + C_5$) | 46.9 | 5.3 |
| TBA | 18.0 | 93.7 |
| DIB | 35.1 | 1.0 |

[1]Feed analysis wt. %: isobutane-14.84; n-butane-7.91; butene-1-10.51; trans-butene-2-16.44; cis-butene-2-7.79; isobutene-41.62
[2]Differential pressure is measure as % change in pressure in normal distillation pressure in catalyst zone and when totally flooded with liquid in catalyst zone.

The invention claimed is:

1. A process for the production of tertiary alcohols comprising:
    (a) feeding water to a distillation column reactor containing a bed of an acid cation exchange resin, said water being fed at a point above said bed;
    (b) concurrently feeding a hydrocarbon stream containing an isoolefin to said distillation column reactor at a point below said bed;
    (c) concurrently in said distillation column reactor:
        (1) contacting said stream and said water with said acid ion exchange resin thereby reacting a portion of said isoolefin with said water to form a mixture containing a tertiary alcohol, unreacted water and unreacted isoolefin;
        (2) separating said tertiary alcohol from said unreacted water and unreacted isoolefin by fractional distillation;
    (d) withdrawing said tertiary alcohol from said distillation column reactor at a point below said bed;
    (e) withdrawing unreacted hydrocarbon from said distillation column reactor at a point above said bed; and
    (f) measuring the amount of water in the alcohol fraction in the lower part of the column and adjusting the water feed rate to maintain that amount above zero but below the azeotropic concentration at the temperature and pressure within the column.

2. The process of claim 1 where a portion of said unreacted hydrocarbon is condensed and returned to said distillation column reactor as reflux.

3. The process of claim 1 wherein a liquid level is maintained in said bed to insure wetting of the catalyst to maintain it in the hydrated state.

4. The process of claim 1 wherein said isoolefin is isobutylene and said tertiary alcohol is tertiary butyl alcohol.

5. The process of claim 1 wherein said isoolefin is isoamylene and said tertiary alcohol is isoamyl alcohol.

6. The process of claim 1 wherein said distillation column reactor is operated a pressure in the range of 15 to 300 psig and a temperature in the bed of 120° to 250° F.

7. The process of claim 6 wherein the pressure in said distillation column reactor is between 25 and 225 psig.

8. The process of claim 7 wherein the temperature within said bed is from 140° F. to 185° F.

9. A process for the production of tertiary alcohols comprising:
  (a) feeding water to a distillation column reactor containing a bed of an acid cation exchange resin, said water being fed at a point above said bed;
  (b) concurrently feeding a hydrocarbon stream containing an isoolefin to said distillation column reactor at a point below said bed;
  (c) concurrently in said distillation column reactor:
    (1) contacting said stream and said water with said acid ion exchange resin thereby reacting a portion of said isoolefin with said water to form a mixture containing a tertiary alcohol, unreacted water and unreacted isoolefin;
    (2) separating said tertiary alcohol from said unreacted water and unreacted isoolefin by fractional distillation;
  (d) restricting the downward flow of internal reflux at selected points in said reaction distillation zone to maintain a liquid level above the restriction for additional contact and reaction of the liquid and distillation vapors;
  (e) withdrawing said tertiary alcohol from said distillation column reactor at a point below said bed;
  (f) withdrawing said unreacted hydrocarbon from said distillation column reactor at a point above said bed; and
  (g) measuring the amount of water in the alcohol fraction in the lower part of the column and adjusting the water feed rate to maintain that amount above zero but below the azeotropic concentration at the temperature and pressure within the column.

10. The process of claim 9 wherein said isoolefin is isobutylene and said tertiary alcohol is tertiary butyl alcohol.

11. The process of claim 9 wherein said isoolefin is isoamylene and said tertiary alcohol is isoamyl alcohol.

12. The process of claim 9 wherein said distillation column reactor is at a pressure between 155 and 300 psig.

13. The process of claim 12 wherein said distillation column reactor is at a temperature within said bed of from 120° F. to 250° F.

14. A method for separating isoolefins from a mixture containing osoolefins and normal olefins comprising:
  (a) feeding water to a distillation column reactor containing a bed of an acid cation exchange resin, said water being fed at a point above said bed;
  (b) concurrently feeding a mixture containing an isoolefin and the corresponding normal olefin to said distillation column reactor at a point below said bed;
  (c) concurrently in said distillation column reactor:
    (1) contacting said mixture and said water with said acid ion exchange resin thereby reacting a portion of said isoolefin with said water to form a tertiary alcohol;
    (2) separating said tertiary alcohol from said normal olefin, unreacted water and unreacted isoolefin by fractional distillation;
  (d) measuring the amount of water in the alcohol fraction in the lower part of the column and adjusting the water feed rate to maintain that amount above zero but below the azeotropic concentration at the temperature and pressure within the column.
  (e) restricting the downward flow of internal reflux at selected points in said reaction distillation zone to maintain a liquid level above the restriction for additional contact and reaction of the liquid and distillation vapors;
  (f) withdrawing said tertiary alcohol from said distillation column reactor at a point below said bed; and
  (g) withdrawing said normal olefin from said distillation column reactor at a point above said bed.

* * * * *